US005700644A

United States Patent [19]
Gould et al.

[11] Patent Number: 5,700,644
[45] Date of Patent: Dec. 23, 1997

[54] IDENTIFICATION OF DIFFERENTIALLY EXPRESSED GENES

[75] Inventors: Michael N. Gould; Eric A. Ariazi, both of Madison, Wis.

[73] Assignee: Wisconsin Alumni Research Foundation, Madison, Wis.

[21] Appl. No.: 480,597

[22] Filed: Jun. 7, 1995

[51] Int. Cl.[6] .................................. C12Q 1/68; C12P 19/34; C12N 15/10; C12N 15/70
[52] U.S. Cl. ...................... 435/6; 435/91.51; 435/172.3; 435/320.1; 435/915; 435/91.2
[58] Field of Search ........................ 435/6, 91.2, 172.3, 435/320.1, 91.51, 91.5

[56] References Cited

U.S. PATENT DOCUMENTS 5,580,726 12/1996 Villeponteau et al. ................. 435/6

OTHER PUBLICATIONS

Hakvoort et al., "Identification of enriched sequences from a cDNA subtraction–hybridization procedure", Nucleic Acids Res. 22: 878–879, Mar. 1994.

Z. Wang, et al., *A gene expression screen*, 88 Proc. Natl. Acad. Sci. U.S.A. 11505–11509 (1991).

P. Liang et al., *Differential Display of Eukaryotic Messenger RNA By Means OF The Polymerase Chain Reaction*, 257 Science 967–971 (1992).

E. Arizai et al., *Cloning Of cDNAs Differentially Expressed Between Regressing And Non–regressing Rat Mammary Carcinomas Induced By Monoterpenes*, 35 Proc. Annu. Meet. Am. Assoc. Cancer Res. (Mar. 1994).

N. Hasan et al., *An MboII/FokI Trimming Plasmid Allowing Consecutive Cycles Of Precise 1–To 12–Base–Pair Deletions In Cloned DNA*, 82 Gene 305–311 (1989).

N. Hasan et al.,*A Novel Multistep Method For Generating Precise Unidirectional Deletions Using Bspmi, A Class–IIS Restriction Enzyme*, 50 Gene 55–62 (1986).

Primary Examiner—Jasemine C. Chambers
Assistant Examiner—Scott D. Priebe
Attorney, Agent, or Firm—Quarles & Brady

[57] ABSTRACT

Methods are disclosed to identify differentially expressed genes. In one aspect, one uses subtractive hybridization to enrich for candidate genes, followed by a PCR amplified radiolabeled display of cDNA products of the hybridization. Specially modified primer binding regions are used that can be achieved either through use of trimming plasmids or non-symmetric display plasmids.

6 Claims, 3 Drawing Sheets

IDENTIFICATION OF DIFFERENTIALLY EXPRESSED GENES

This invention was made with United States government support awarded by ARMY, DOD Grant # DAM 17-94-J4041 and NIH Grant #'s CA38128 and CA09471. The United States Government has certain rights in this invention.

BACKGROUND OF THE INVENTION

1. Field of the Invention

This invention relates to cloning and identification of over- and under-(differentially) expressed genes in experimental relative to control cells. It appears especially well suited to assist in determining the gene expression effects of candidate drugs, in identifying target genes for developmental biology, and in discovering of markers for diagnostic purposes.

2. Background of the Art

Researchers developing therapies for diseases often want to know what effect a treatment will have at the molecular level (that is, which genes are turned on or off at the level of transcription as a result of therapy). In the past, to answer this question they have isolated mRNA from experimental and control tissues, and generated cDNA libraries from them. From this point, two techniques were developed for approaching this problem, "subtractive hybridization" and "differential display".

In subtractive hybridization, cDNA clones that were common to both treated and control tissues were selected out by hybridizing to each other, leaving differentially expressed cDNA clones. See Z. Wang et al., 88 P.N.A.S. USA 11505–11509 (1991). The disclosure of this article, and of all other publications recited herein, are incorporated by reference as if fully set forth.

The subtractive hybridization method of Wang et al. removes commonly expressed cDNA from the experimental and control cDNA pools and thereby enriches for differentially expressed genes. However, thereafter cloning the candidate differentially expressed genes is very laborious and time consuming (on the order of many months to years), especially if one wishes to confirm identification of genes that are up-regulated or down-regulated, but not expressed in as great quantities as other differentially expressed genes. Cloning such differentially expressed cDNAs involves cycles of classical probe hybridization experiments to isolate only a few clones at a time, followed by subtracting the recently cloned cDNAs from the library, and then repeating the cloning cycle until the library is completely screened. This may take 30–40 or more cloning cycles, and months to more than a year of work.

The "differential display" technique of P. Liang et al., 257 Science 967 (1992) is much faster, but has its own problems. Subsets of cDNAs are partially amplified by using a 3' anchor primer to the poly(dT) tail, plus two additional arbitrary bases, thus selecting for partial 1/16 subsets of cDNAs. The original 5' primer for the PCR technique was a short 9 or 10 base oligomer of arbitrary sequence that randomly annealed upstream somewhere internally along the gene, and thus determined the size of the PCR product.

Because the original primers are small (to avoid missing most sequences), a very low annealing temperature is required. This can give rise to poor reproducibility between identical reactions, and can contribute to some false positives. Furthermore, because the libraries used with this technique contain commonly expressed cDNAs (which comprise the vast majority of the cDNA population) there exists a high level of background noise. Also, the technique can miss some differentially expressed genes (e.g. when a gene does not contain a sequence similar to the arbitrary internal 5' primer to allow binding). Using this technique with longer primers (e.g. 20 bases) and varied stringency conditions has helped reproducibility somewhat, but not resolved the method's other problems.

In E. Ariazi et al., 35 Proc. Annu. Meet. Am. Assoc. Cancer Res. A 3715 (March 1994), we proposed a multistep technique involving subtractive hybridization followed by a differential display applied to the subtracted libraries. While this technique was an improvement (e.g. reduced background noise), it still did not teach how to identify all differentially expressed genes and still suffered from reproducibility problems.

It can therefore be seen that a need exists for an improved method of identifying differentially expressed genes.

SUMMARY OF THE INVENTION

In one aspect the invention provides a method for identifying differentially expressed genes in experimental cells relative to control cells. One forms a first cDNA library from RNA that has been expressed by the experimental cells and a second cDNA library from RNA that has been expressed by the control cells. One then selects out at least a portion of the cDNA common to both the first and second libraries by subtractive hybridization to enrich for cDNA coding for the differentially expressed genes.

Thereafter, one amplifies the enriched cDNA using polymerase chain reaction (preferably with labeled—radiolabelled; fluorescent labelled—nucleotides) to create amplified (preferably labelled) DNA, and displays the amplified DNA on a chromatography gel to separate different DNA coding for different differentially expressed DNA. In accordance with the invention at least partially during the polymerase chain reaction the enriched cDNA has attached thereto known 5' and 3' DNA PCR primer binding regions positioned 5' and 3' respectively of cDNA coding for cell m-RNA, and the DNA PCR primer 5' and 3' binding regions are different from each other.

In a preferred form, the subtractive hybridization separately enriches for cDNA coding for underexpressed genes and cDNA coding for overexpressed genes, and thereafter both enriched cDNA substractive hybridization products are separately so amplified and separately so displayed, and the displays are then compared to each other to select out common gel positions (and thus select for unique gel positions).

In one variant, the enriched cDNA has been inserted into a trimming plasmid and trimmed at one end prior to the amplification step (after the hybridization step), or in the alternative prior to the subtractive hybridization the cDNAs have been provided with different 5' and 3' DNA ends corresponding to the PCR primer binding regions.

In another aspect, the invention involves creating two separate cDNA libraries that are derived from the experimental cells and control cells respectively, where the cDNA in both libraries have known 5' and 3' DNA PCR primer binding regions positioned 5' and 3' respectively of the cDNA that codes for cell m-RNA. The DNA PCR primer 5' and 3' binding regions are different from each other. Thereafter, one separately amplifies each cDNA library using polymerase chain reaction (preferably with labelled nucleotides) to create amplified (preferably labelled) DNA.

One then displays the labelled amplified DNA derived from each library in a separate chromatography gel lane, and compares the DNA positions in a first such lane with those in a second such lane to select for cDNAs having unique lane positions.

It will be appreciated that a key feature of the invention is the provision of known, different PCR primer binding sites outside of the cell DNA, either by use of a trimming plasmid acting on a linker, or by addition of different linker ends prior to hybridization. Given this, and the use of the fragmented subtractive hybridization products for PCR, the amplification can proceed across the entire DNA. Further, use of larger primers is made possible by this, and thus high stringency PCR conditions. Reproducibility problems are thus reduced.

The objects of the invention therefore include providing methods of the above kind:

(a) that can identify over and under expressed DNA;
(b) that reduce background noise;
(c) that can quickly identify over-expressed and under-expressed genes that have relatively small expression;
(d) that provide reproducible results; and
(e) that maximize the likelihood of identifying all differentially expressed genes.

These and still other objects and advantages of the present invention will be apparent from the description which follows. However, the description which follows is only of the preferred embodiments. The claims should therefore be looked to in order to assess the full scope of the invention.

DETAILED DESCRIPTION OF THE PREFERRED EMBODIMENTS

General Overview

Figure 1:
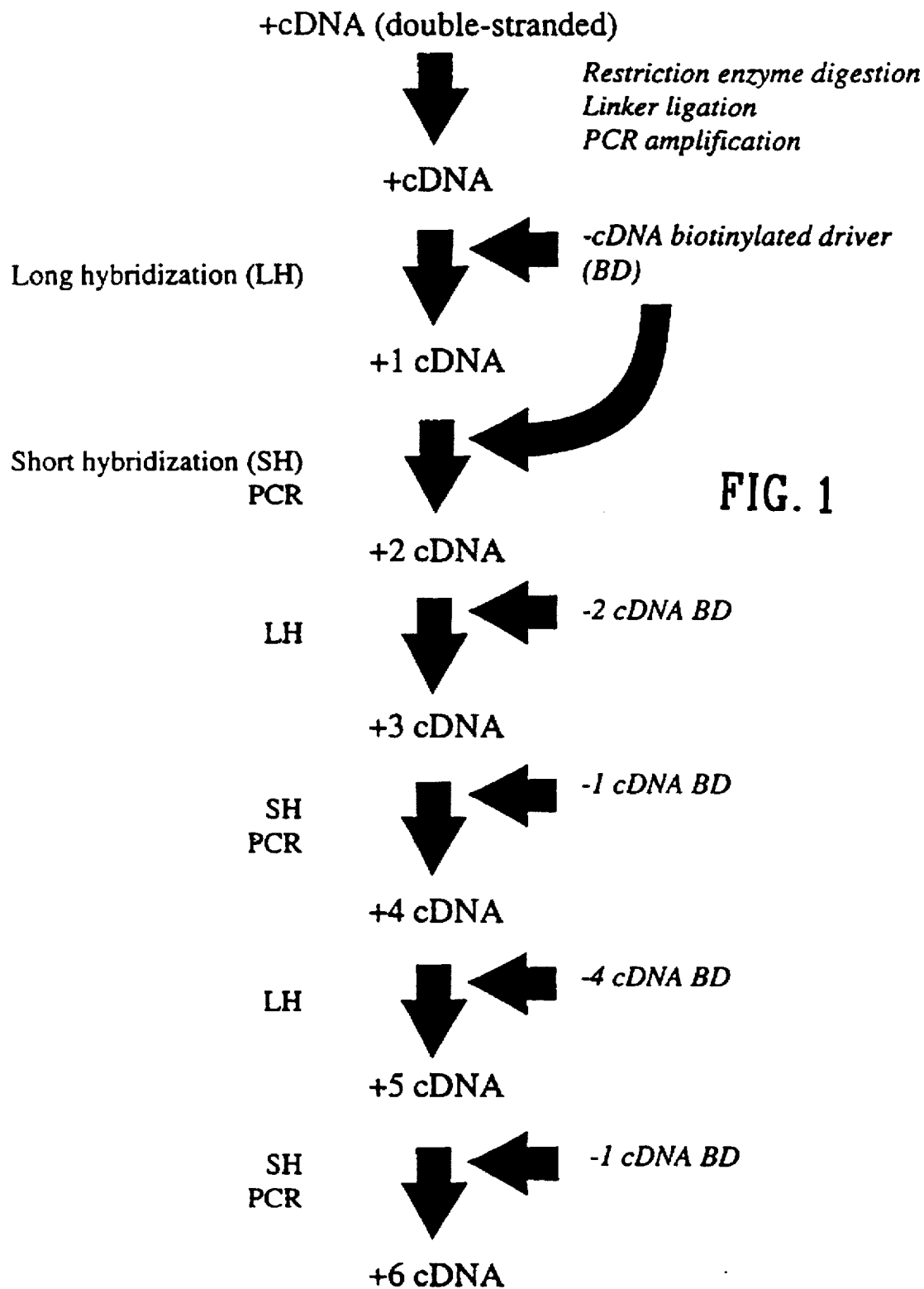
FIG. 1 is a schematic depiction of subtractive hybridization.

We first isolate mRNA from experimental and control tissues for generation of cDNA. The resulting cDNA populations usually differ essentially only in differential expression of target genes associated with the experimental protocol. Subtractive hybridization (FIG. 1) between the two cDNA populations removes most common cDNAs and enriches for differentially expressed cDNAs.

The subtractive hybridization procedure includes initial cDNA fragmentation, followed by attachment to linkers having known identical PCR binding regions, polymerase chain reaction (PCR) amplification, followed by subtractive hybridization (hybridizing DNA and then separating out common unwanted DNA). After a number of cycles, and after a FIG. 3 modification, enriched subpopulations of cDNAs are PCR amplified and displayed on a sequencing gel (FIG. 2) using special primers. Unique individual cDNA fragments are excised and reamplified for subsequent characterization.

In accordance with one embodiment of the invention, prior to display amplification, we cloned the subtracted library into a trimming plasmid and allowed three rounds of trimming to occur at the 5' linker end to insure that the 5' and 3' ends were different from each other. We designed primers for the PCR amplification based on the trimming plasmid sequence on each side of the cDNA insert. Thus a PCR primer for the 5' end consisted of the 14 bp from the trimming cassette plus any two other bases, so that the primer overlapped a cDNA fragment by 2 bases. The 3' primer was the 17 bp sequence adjacent to the other end of the cloned insert (containing base pairs from the original subtraction hybridization linker, an EcoRI site, and a portion of the trimming plasmid).

In the alternative, we could use a special pDisplay linker plasmid prior to the hybridization. The plasmid has an insertion site bounded by different PCR regions. By inserting the cDNA in these plasmids one adds asymmetrical known PCR primer binding regions to the system.

In either technique, the labelling PCR can be performed with primers of 15 or more bases (e.g. 16/17), thus allowing use of the highest temperature which still permits PCR to proceed. This leads to high specificity and reproducible results. The libraries can be completely screened in 16 sets of reactions since the DNA is shorter and the 5' primer now flanks the sequence (and is not internal to it). The products are resolved and excised on a polyacrylamide gel for subsequent PCR amplification, subcloning, and characterization.

In either variant, poly(A)+RNA can be isolated from experimental and control cells using the PolyATract System 1000 (Promega) following manufacturer's directions. The PolyATract System 1000 works by hybridizing a biotinylated oligo (dT) probe to mRNA concurrently with removal of cellular debris. mRNA-oligo (dT) complexes are subsequently bound to streptavidin paramagnetic particles and captured with a magnet.

The Superscript Choice System for cDNA Synthesis (Gibco BRL Life Technologies) is used for double stranded cDNA synthesis from poly(A)+RNA. This system was chosen because it uses a moloney murine leukemia virus reverse transcriptase engineered to lack RNase H activity (Superscript RT), resulting in a higher frequency of full length cDNAs.

cDNA synthesized from experimental and control cells are termed +cDNA and −cDNA, respectively. A portion of the +cDNA and −cDNA is reserved for construction of nonfragmented cDNA plasmid libraries with the vector pSport1 and Electromax Efficiency DH12S *E. coli* host cells (Gibco BRL Life Technologies). A plasmid library provides greater ease of clone manipulation. Libraries are amplified and stored, and the remaining +cDNA and −cDNA reserved for use in gene expression screens.

As an example below, we use our technique to test the effect of a terpene (e.g. limonene) on mammary (rat) carcinomas. Limonene is known to assist in mammary carcinoma regression. Our technique is, however, intended to be useful with a wide range of hosts (e.g. other mammals such as humans), with a wide variety of cell types therefrom (diseased; healthy; lymphocyte; etc.), and where the hosts have been presented with a wide variety of test challenges.

EXAMPLE I

A. Hybridization.

Two resulting cDNA populations from experimental (limonene treated) mammary carcinomas (+cDNA) and control (not treated) mammary carcinomas (−cDNA) shall both serve as "driver" and "tracer" DNA for the subtractive hybridization process. For the enrichment of genes that are up-regulated in experimental carcinomas (FIG. 1 shows enrichment for up-regulated genes), +cDNA (tracer) is subtracted with biotinylated ("driver") −cDNA. In the opposite parallel experiment (not shown), −cDNA is subtracted with biotinylated +cDNA. This is performed to enrich for cDNAs down-regulated in experimental carcinomas. Thus, subtracted +cDNA is enriched for experimental-induced target genes, and subtracted −cDNA is enriched for experimental-repressed target genes.

Except as noted below with regard to the modified linker for the alternative "pDisplay" linker technique, the FIG. 1 subtractive hybridization technique follows the teachings of Z. Wang et al., 88 P.N.A.S. USA 11505–11509 (1991). As shown in FIG. 1, we fragment the +cDNA with restriction endonucleases (e.g. Alu I and Alu I plus Rsa I). (If desired, one could instead use a type IIs restriction enzyme (which cuts a fixed distance from the site) to remove some of the bias of the selection of the enzyme.) We then ligate (on both termini of the fragments) 21 bp oligodeoxynucleotide linkers having a 5' blunt end and a 4-base 3' overhang as described in Wang. The flush end contains an EcoRI site.

Following linker ligation, the fragmented cDNAs undergo PCR amplification using the 21 bp linkers as primer regions. cDNA fragments that are common to both +cDNA and −cDNA populations amplify substantially equally, while different cDNA fragments within a population should be differentially amplified.

As schematically shown in FIG. 1, 50 µg of −cDNA can be completely digested with EcoRI to suppress contaminating cDNA from being amplified. −(driver)cDNA is then photobiotinylated and combined with 2.5 µg non-biotinylated +(tracer)cDNA. The mixture is completely denatured by boiling and then cooled to 68° C. for a long hybridization (20 hours). Addition of streptavidin leads to formation of streptavidin—biotin—DNA complexes that are readily removed by several phenolchloroform extractions.

Subtracted +cDNA (termed +1cDNA) can then again be subtracted using 25 µg biotinylated −cDNA, this time for a short hybridization (SH) of 2 hours, yielding +2cDNA. The parallel under-expressed experiments are simultaneously conducted. +2cDNA and −2cDNA are then PCR amplified using the known linker sequences. 2.5 µg non-biotinylated +2cDNA is then subtracted against 50 µg EcoRI treated—biotinylated driver −2cDNA for a long hybridization followed by 25 µg driver of −1cDNA for a short hybridization, resulting in +4cDNA, which is then PCR amplified. Another similar cycle is performed giving +6cDNA (and in the parallel experiment −6cDNA). Thus far we have followed the Wang et al. technique.

B. Trimming.

However, in accordance with one embodiment of the present invention, the subtracted cDNA libraries are next reconfigured and optimized for the display step. As noted above, during construction of the libraries both ends of the cDNA fragments were ligated to the same linker, i.e. the ends are symmetrical. Also, the first few bases at both ends of the cDNA fragments are not random. They reflect the restriction enzyme used to make the cDNA. In order to remedy these problems and make the construction suitable for our display technique, the linker and several adjacent cDNA base pairs from one end of each cDNA is removed and replaced with a new PCR priming sequence. This is accomplished by using the EcoRI site within the cDNA libraries' linker (deletes 9 bp) to permit cloning of the libraries into a trimming plasmid, termed pTRIM14.

pTRIM14 (FIG. 3) contains a cassette designed with BseRI and BsgI 6 bp recognition sites to facilitate multistep consecutive cycles of precise unidirectional 14 bp deletions of cloned DNA. BseRI and BsgI are class-IIS restriction enzymes and cleave DNA downstream of their recognition sites to generate staggered ends at 10/8 and 16/14 nucleotides (n+), respectively. These recognition site sequences are arranged into a BseRI/BsgI trimming cassette such that the BseRI site is at the 5' end directly adjacent to the BsgI site at the 3' end and subcloned into the multiple cloning site (MCS) of pUC18 (Gibco BRL Life Technologies), yielding pTRIM14.

pTRIM14 was constructed as follows: the oligonucleotides TRIM14α (SEQ ID NO: 1) and TRIM14β (SEQ ID NO:2) were synthesized (University of Wisconsin Biotechnology Center, Madison, Wis. USA) and annealed at 37° to form a BseRI/BsgI trimming cassette with 5' HindIII and 3' EcoRI staggered ends. The intervening sequence between the HindIII and EcoRI sites in the MCS of pUC18 were removed by restriction digestion. The resulting linearized plasmid was ligated to the BseRI/BsgI cassette to give pTRIM14.

Precise unidirectional deletions were then generated into the subtracted cDNA libraries subcloned within pTRIM14 just downstream of the trimming cassette by three deletion or trimming cycles. The trimming cycle (FIG. 3) begins by stepwise digestion first with BsgI and then BseRI to produce cuts 16/14 nt distal and 4/2 nt proximal, respectively, relative to the 3' end of the cassette, thus conserving the trimming cassette but cutting into the 5' end of the cDNA fragment. The trimming cycle proceeds by treatment with Mung Bean nuclease to blunt end the linearized DNA and finally recircularization with T4 DNA ligase back into a plasmid. Each trimming cycle results in a precise 14 bp deletion.

Figure 3:
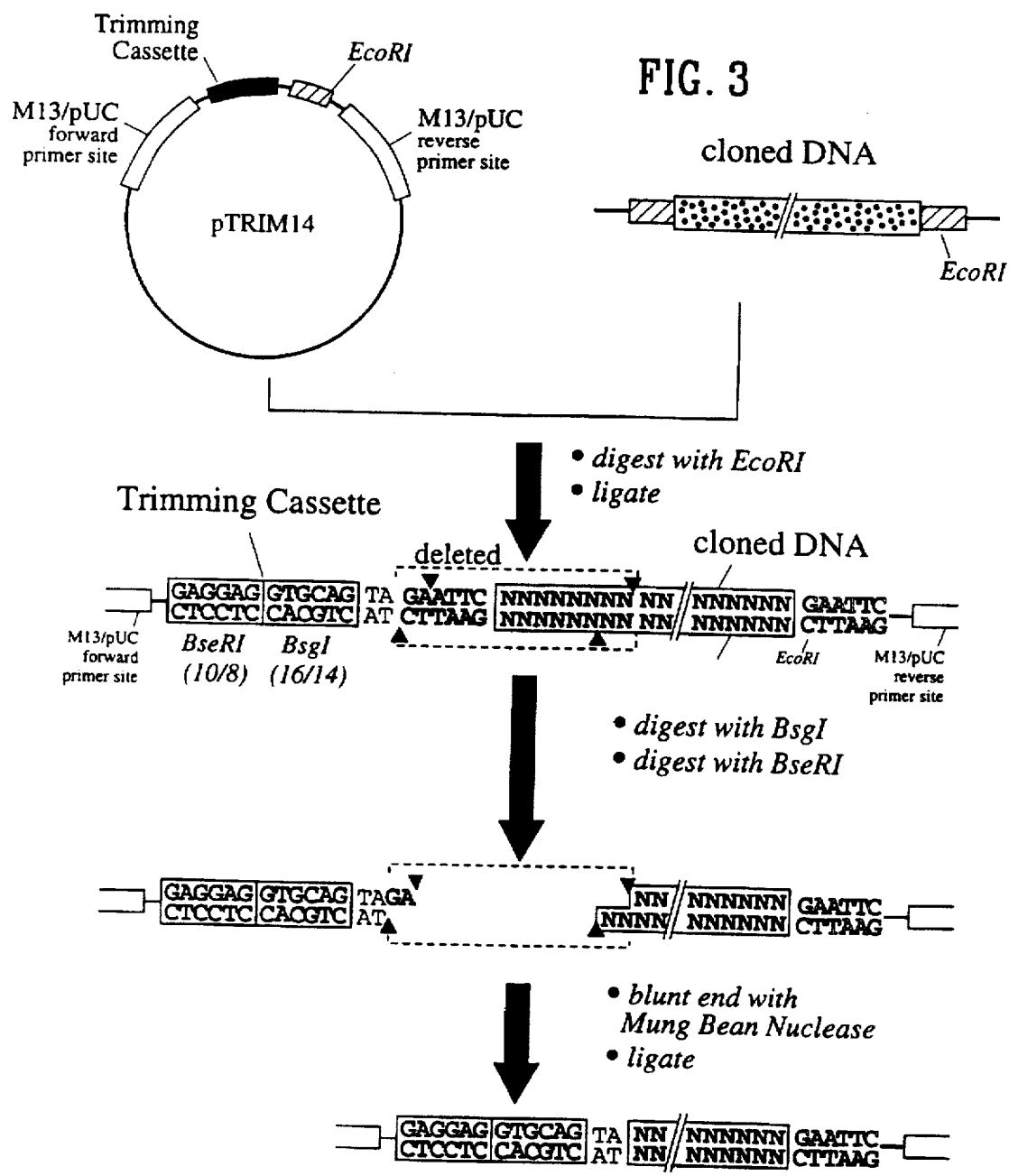
FIG. 3 is a schematic depiction how a trimming plasmid can be used to modify hybridization product. It shows the use of SEQ ID NO:8 and SEQ ID NO:9.

This cycle is repeated two additional times for a total of three cycles and deletion of 42 bp (FIG. 3). In the end, the linker on the left end of the cDNA libraries was completely removed plus an additional 30 bp, leaving randomized cDNA sequence. Furthermore, cDNA fragments that may contain BsgI or BseRI are not lost from the library since a portion of the cDNA fragment is retained.

C. Display.

Figure 2:
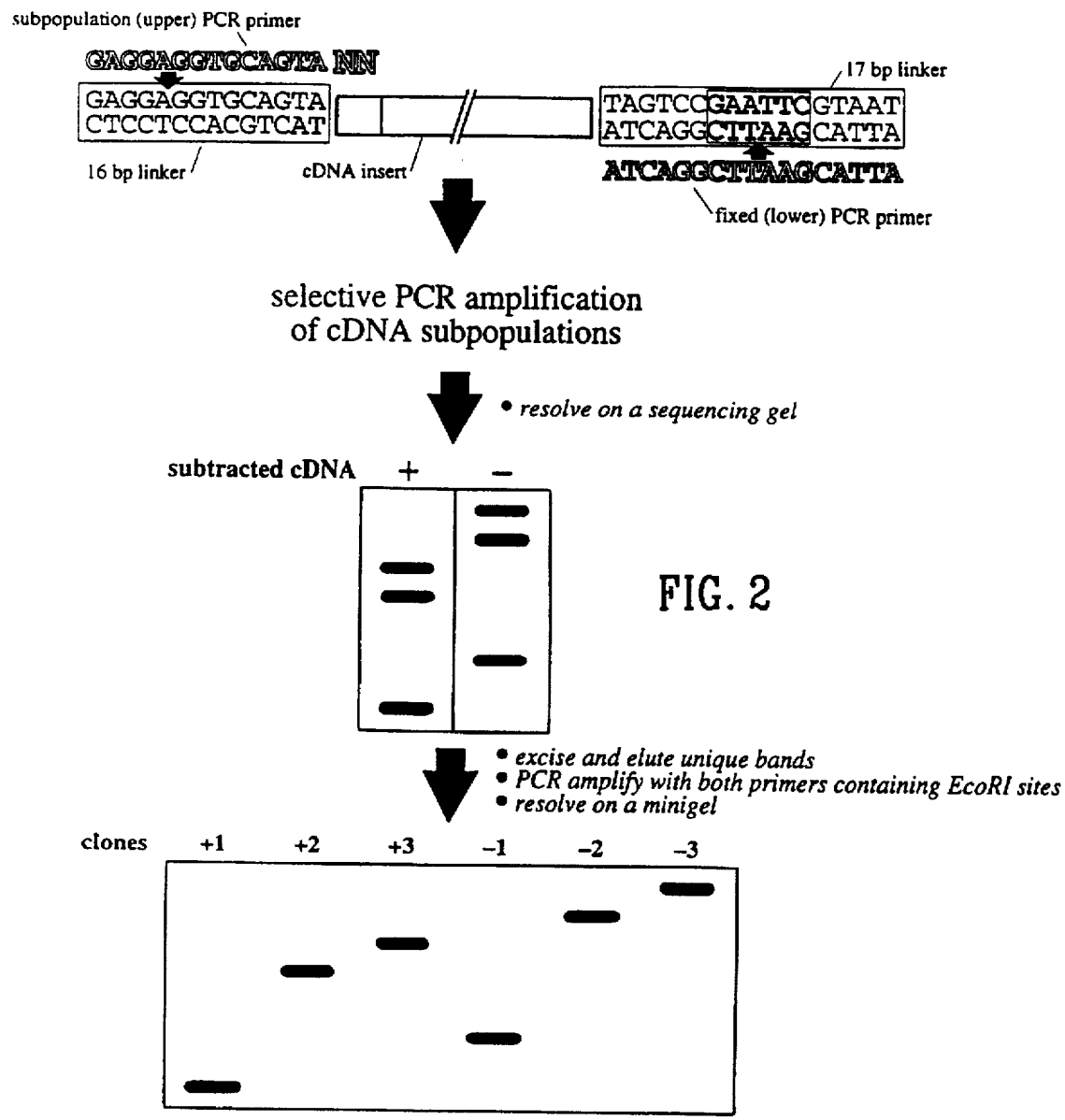
FIG. 2 is a schematic depiction of a display technique using modified subtractive hybridization product as a starting material. It shows the use of SEQ ID NO:3 and SEQ ID NO:4.

In accordance with the invention, the reconfigured subtracted cDNA libraries are then displayed by amplification of cDNA subpopulations using 16 sets of PCR primers. (FIG. 2). In each primer set, one primer is always the same or fixed and anneals at the unmodified or right end of the cDNA fragment. This fixed primer is a 17-mer with a sequence of (SEQ ID NO:3) and is composed 5'–3' of a pTRIM14 sequence, an EcoRI site (underlined), and original linker sequence. The second primer in each primer set anneals on the randomized or left end of the cDNA fragment and is termed the subpopulation primer. The 5' end of the subpopulation primer anneals to 14 bp of pTRIM14 sequence and its 3' end overlaps the cDNA fragment by 2 bp. These two 3' bases in each individual subpopulation primer will consist of 1 of the 16 possible 2 base combinations resulting in a subpopulation primer sequence of (SEQ ID NO:4). Therefore, one set of a total of sixteen sets of PCR primers results in selective annealing and amplification of a subpopulation of the cDNA, and consecutive amplification with each of the sixteen sets of primers allows complete screening of the libraries. It will be appreciated that the entire tested cDNA will now be amplifiable because the lengths are truncated before the hybridization and because both ends are now fixed, different, and known. Further, the long primer binding sites now permit the use of high stringency PCR.

PCR products of +6Δ3cDNA and −6Δ3cDNA (6 rounds of subtraction and 3 cycles of trimming) amplified using each set of primers in the presence of [α-$^{35}$S] dATP are then resolved on a sequencing gel. Most of the resulting bands are unique to one subpopulation of subtracted cDNA. However, if there is mispriming of the two terminal 3' bases of the subpopulation primer those can be selected out by looking for bands common to both. The staggering of the bands along the gel permits immediate recognition of how many differentially expressed genes exist. Thus, small expression genes are not masked by large expression genes.

The differential display conditions of P. Liang et al., 257 Science 967 (1992) are generally suitable for use with our modified starting material, albeit for a different purpose. However, in order to maximize selective amplification and minimize redundancy of clone isolation, the annealing temperature and dNTP concentration of the PCR reaction has been modified to take advantage of the new primers. Annealing temperature of 57°–61° C. (preferably 59° C.) are optimal with 10–20 μM (preferably 15 μM) dNTP.

Reactions were performed with all 16 sets of subpopulation primers. In a reaction volume of 50 μl, PCR products were labelled by adding 10 μCi of [α-$^{35}$S] dATP. The 1X PCR buffer was composed of 50 mM KCl, 10 mM Tris-HCl (pH 8.3), 1.5 mM MgCl$_2$ 0.001% (w/v) gelatin, and the PCR temperature profile used was 94°—5 min hot start followed with 94°—1 min, 59°—1 min, 72°—1 min for 30 cycles and lastly 72°—10 min to insure double stranded cDNA. These experiments were also performed in parallel, omitting the radiolabel and instead silver stained to visualize the bands directly which greatly improves efficiency of band isolation.

Unique bands were excised, eluted from the gel and reamplified using the same fixed PCR primer and a pan primer (instead of subpopulation primer) that now amplifies the entire cDNA population. The pan primer, derived from the subpopulation primer, has an EcoRI site added to the 5' end and the two terminal variable 3' bases removed (SEQ ID NO:5). Isolated cDNA fragments are digested with EcoRI and subcloned into the multiple cloning site of the pSPORT1 plasmid (Gibco BRL Life Technologies). We have isolated bands each from both +6Δ3 and −6Δ3 subtracted cDNA limonene treated cell libraries.

One then sequences these using conventional sequencing. Differential expression of each cloned cDNA fragment can be confirmed and quantitated by Northern blot analysis, RNase protection assays, or other techniques. Expression levels of an isolated test clone (rat YWK-II cDNA), were compared between a panel of at least 5 regressing mammary carcinomas and 5 non-regressing carcinomas and quantitated by densitometric analysis using a phosphorimaging system (Molecular Dynamics), which confirmed the test clone's differential expression.

D. Variations.

It will be appreciated that other variations are also possible. One could instead use an alternative method that will avoid the necessity of reconfiguring the subtracted libraries after hybridization. In this variant, before the hybridization step, the cDNA libraries are fragmented using class IIs restriction enzymes to yield PCR compatible lengths. The cDNA fragmented libraries are then ligated into pDisplay plasmid, having unique, known, and different 5' and 3' priming sequences flanking the insert point. This adds the desired primers at the beginning of the method. One then proceeds as before, albeit without the trimming plasmid step.

As an example, before subtraction, the cDNA libraries are fragmented using the class IIs restriction enzymes FokI and MboII, because as class IIs endonucleases, they cut downstream of their recognition sites resulting in non-biased sequence at the cDNA fragment ends. Next, the cDNA fragmented libraries are ligated into the EcoRV site of the plasmid pDisplay. pDisplay can be constructed by digestion of pUC19 (Gibco BRL Life Technologies) with EcoRI followed by ligation to the annealed oligonucleotides DISPLAYα (SEQ. ID No. 6) and DISPLAYβ (SEQ. ID No. 7) which provide the linker sequences. The linker sequences contain the restriction sites 5' to 3' EcoRI, KpnI, MboII, EcoRV, HindIII, FokI, (in reverse orientation) and EcoRI. The EcoRV site is centrally located, such that digestion of pDisplay with EcoRV results in a linearized plasmid with blunt ends.

Subsequently, ligation of linearized pDisplay with the fragmented cDNA libraries results in a unique linker at each cDNA end. The linkers were designed to facilitate unique priming sites at each end of the cDNA fragments, using one site as a fixed primer (no cDNA fragment overlap) and the other as a subpopulation primer (2 bp cDNA fragment overlap), analogous to the first version described above. Furthermore, a MboII site and an FoKI (reverse orientation) site in the left and right linkers, respectively, facilitates linker removal since they are class IIs restriction enzymes, if it becomes necessary. Additionally, the linkers contain HindIII, EcoRI, and KpnI sites for efficient subcloning of isolated cDNA fragments.

We have tested the second version using the mouse neuroblastoma cell line, Neuro-2A, that morphologically differentiates by developing neurite outgrowths when treated with the monoterpene perillyl alcohol. We have isolated the mouse ornithine transcarbamylase (OTC) gene as a putative induced gene and the mouse embryonal carcinoma F9 cell cDNA as a putative repressed gene.

It should be understood that other variations to the technique are also intended to be within the claims. For example, the hybridization step can be skipped, with a modified cDNA library being used as starting material for the display step. While this may complicate the gel separation somewhat, it would still be an improvement over prior art differential display techniques.

We claim:

1. A method for identifying differentially expressed genes in experimental cells relative to control cells, comprising:

forming a first cDNA library from RNA that has been expressed by the experimental cells and a second cDNA library from RNA that has been expressed by the control cells, wherein individual members of the cDNA libraries are comprised of a 5' linker, a cDNA, and a 3' linker, wherein all members of said first cDNA library have the same 5' linker and 3' linker, all members of said second cDNA library have the same 5' linker and 3' linker, and within each library the 5' linker is different than the 3' linker;

removing from the libraries at least a portion of the cDNA common to both the first and second libraries by subtractive hybridization to provide enriched cDNA coding for differentially expressed genes that are present in said libraries;

wherein for each library individual members of the enriched cDNA derived from that library comprise a 5' DNA PCR (polymerase chain reaction) primer binding region and a 3' DNA PCR primer binding region said 5' and 3' DNA PCR primer binding regions comprising said 5' linker and said 3' linker, respectively, and up to no more than two nucleotides of cDNA adjacent to the respective linkers;

thereafter amplifying the enriched cDNA by PCR;

displaying the amplified DNA on a chromatography gel to separate different DNA; and thereafter analyzing the gel to identify differentially expressed genes.

2. The method of claim 1, wherein labelled nucleotides are incorporated into the amplified, enriched cDNA during the amplification step.

3. The method of claim 1, wherein the subtractive hybridization step separately enriches for cDNA differentially expressed in each library, and thereafter enriched cDNA hybridization products from each library are separately so amplified and separately so displayed, and the displays are compared to each other to identify chromatography positions having different amounts of amplified DNA.

4. A method for identifying differentially expressed genes in experimental cells relative to control cells, comprising:

creating two separate cDNA libraries that are derived from the experimental cells and control cells respectively, wherein individual members of the cDNA libraries are comprised of a 5' PCR (polymerase chain reaction) primer binding region, a cDNA, and a 3' PCR primer binding region, with the 5' PCR primer binding region within a library being the same for the members of that library, the 3' PCR primer binding region within a library being the same for the members of that library, and within each library the 5' and 3' primer binding regions are different from each other in that library, with said primer binding regions each being made up of nucleotides that are not part of the cDNA sequence and up to no more than two nucleotides of the cDNA sequence adjacent thereto;

thereafter separately amplifying each cDNA library using polymerase chain reaction;

thereafter displaying the amplified DNA derived from each library in separate chromatography gel lanes; and thereafter comparing DNA positions in a first such lane with those in a second such lane to select for cDNAs having in lane positions different amounts of amplified DNA.

5. A method for identifying differentially expressed genes in experimental cells relative to control cells, comprising:

forming a first cDNA library from RNA that has been expressed by the experimental cells and a second cDNA library from RNA that has been expressed by the control cells;

removing from both of the libraries at least a portion of the cDNA common to both the first and second libraries by subtractive hybridization to provide enriched cDNA coding for differentially expressed genes that are present in the libraries;

separately inserting the enriched cDNA derived from each library into trimming plasmids and for both libraries trimming the enriched cDNA from at least one end such that the resulting trimmed cDNA from both libraries has 5' and 3' DNA PCR (polymerase chain reaction) primer binding regions at least partially 5' and at least partially 3' respectively of cDNA that codes for cell mRNA, wherein DNA PCR primer 5' binding regions and 3' binding regions for both libraries are different from each other within a trimmed cDNA library;

thereafter separately amplifying the enriched, trimmed cDNA from both libraries using polymerase chain reaction;

displaying the amplified DNA on a chromatography gel to separate different DNA coding for different differentially expressed DNA;and analyzing the gel to identify chromatography positions having different amounts of amplified DNA, and to thereby identify differentially expressed genes.

6. The method of claim 5, wherein labelled nucleotides are incorporated into the amplified, enriched cDNA during the amplification step.

* * * * *

SEQUENCE LISTING ( 1 ) GENERAL INFORMATION:

( i i i ) NUMBER OF SEQUENCES: 9

-continued ( 2 ) INFORMATION FOR SEQ ID NO:1:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:1:

AGCTTGAGGA GGTGCAGTAG                                              20

( 2 ) INFORMATION FOR SEQ ID NO:2:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:2:

AATTCTACTG CACCTCCTCA                                             20

( 2 ) INFORMATION FOR SEQ ID NO:3:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:3:

ATTACGAATT CGGACTA                                                   17

( 2 ) INFORMATION FOR SEQ ID NO:4:

( i ) SEQUENCE CHARACTERISTICS:
        ( A ) LENGTH: 16 nucleotides
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:4:

GAGGAGGTGC AGTANN                                                     16

( 2 ) INFORMATION FOR SEQ ID NO:5:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:5:

CCGAATTCGA GGAGGTGCAG TA                                         22

( 2 ) INFORMATION FOR SEQ ID NO:6:

( i ) SEQUENCE CHARACTERISTICS:
        ( A ) LENGTH: 34 nucleotides (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:6:

AATTCGGTAC CGAAGAGATA TCAAGCTTCA TCCG          34

(2) INFORMATION FOR SEQ ID NO:7:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:7:

AATTCGGATG AAGCTTGATA TCTCTTCGGT ACCG          34

(2) INFORMATION FOR SEQ ID NO:8:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

GAGGAGGTGC AGTAGAATTC NNNNNNNNNN          30

(2) INFORMATION FOR SEQ ID NO:9:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

NNNNNNGAAT TC          12